(12) United States Patent
Duchon et al.

(10) Patent No.: US 8,262,610 B2
(45) Date of Patent: Sep. 11, 2012

(54) CATHETER FLUID CONTROL SYSTEM

(75) Inventors: Douglas J. Duchon, Chanhassen, MN (US); Robert F. Wilson, Roseville, MN (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 0 days.

(21) Appl. No.: 12/059,500

(22) Filed: Mar. 31, 2008

(65) Prior Publication Data
US 2008/0183131 A1 Jul. 31, 2008

Related U.S. Application Data

(62) Division of application No. 10/076,895, filed on Feb. 14, 2002, now abandoned.

(60) Provisional application No. 60/268,568, filed on Feb. 14, 2001, provisional application No. 60/269,112, filed on Feb. 15, 2001.

(51) Int. Cl.
*A61M 29/00* (2006.01)
(52) U.S. Cl. .................................................. 604/97.03
(58) Field of Classification Search ............... 604/97.01, 604/97.03, 98.01, 100.01, 100.02, 100.03
See application file for complete search history.

(56) References Cited

U.S. PATENT DOCUMENTS

| | | | | |
|---|---|---|---|---|
| 3,731,679 A | * | 5/1973 | Wilhelmson et al. | 604/121 |
| 3,739,943 A | * | 6/1973 | Wilhelmson et al. | 222/59 |
| 4,512,764 A | * | 4/1985 | Wunsch | 604/80 |
| 4,535,820 A | * | 8/1985 | Raines | 137/854 |
| 4,559,036 A | * | 12/1985 | Wunsch | 604/81 |
| 4,854,324 A | * | 8/1989 | Hirschman et al. | 600/432 |
| 4,888,004 A | * | 12/1989 | Williamson et al. | 604/45 |
| 4,966,199 A | * | 10/1990 | Ruschke | 137/843 |
| 4,966,579 A | * | 10/1990 | Polaschegg | 604/65 |
| 5,021,046 A | * | 6/1991 | Wallace | 604/97.03 |
| 5,084,060 A | * | 1/1992 | Freund et al. | 606/192 |
| 5,152,776 A | * | 10/1992 | Pinchuk | 606/192 |
| 5,171,299 A | * | 12/1992 | Heitzmann et al. | 604/100.03 |
| 5,196,017 A | * | 3/1993 | Silva et al. | 604/97.03 |
| 5,226,886 A | * | 7/1993 | Skakoon et al. | 604/153 |
| 5,249,579 A | * | 10/1993 | Hobbs et al. | 600/458 |
| 5,254,101 A | * | 10/1993 | Trombley, III | 604/207 |
| 5,267,964 A | * | 12/1993 | Karg | 604/141 |
| 5,300,017 A | * | 4/1994 | Isoyama et al. | 600/18 |
| 5,300,027 A | | 4/1994 | Foote et al. | |
| 5,346,470 A | * | 9/1994 | Hobbs et al. | 604/24 |

(Continued)

FOREIGN PATENT DOCUMENTS
EP 0359531 A2 3/1990
(Continued)

*Primary Examiner* — Nicholas Lucchesi
*Assistant Examiner* — Aarti B Berdichevsky
(74) *Attorney, Agent, or Firm* — Shumaker & Sieffert, P.A.

(57) ABSTRACT

A system and method is provided including a fluid communications network that sends priming and waste fluid to a waste bag, obviating the presence of open fluid containers in an operating room or catheter lab. The fluid communications network is constructed and arranged to allow nearly automated priming and bubble removal, thereby reducing the possibility of operator caused errors in set-up and reducing the time required for set-up. The fluid communications network is useable for attachment to a balloon catheter for inflation thereof. In order to provide greater control and automation of the inflation of the balloon catheter, a conversion kit is provided that can be used to convert an existing automatic injector into an injector useable for automatically controlling the small amount of injection fluid typically associated with balloon catheters.

8 Claims, 7 Drawing Sheets

U.S. PATENT DOCUMENTS

| | | | |
|---|---|---|---|
| 5,423,749 A * | 6/1995 | Merte et al. | 604/67 |
| 5,464,388 A * | 11/1995 | Merte et al. | 604/153 |
| 5,494,036 A * | 2/1996 | Uber et al. | 600/432 |
| 5,515,851 A * | 5/1996 | Goldstein | 600/431 |
| 5,569,181 A * | 10/1996 | Heilman et al. | 604/30 |
| 5,573,515 A * | 11/1996 | Wilson et al. | 604/236 |
| 5,599,301 A * | 2/1997 | Jacobs et al. | 604/65 |
| 5,739,508 A * | 4/1998 | Uber, III | 235/375 |
| 5,795,333 A * | 8/1998 | Reilly et al. | 604/154 |
| 5,800,397 A * | 9/1998 | Wilson et al. | 604/151 |
| 5,806,519 A * | 9/1998 | Evans et al. | 600/431 |
| 5,808,203 A * | 9/1998 | Nolan et al. | 73/700 |
| 5,840,026 A * | 11/1998 | Uber et al. | 600/431 |
| 5,843,037 A * | 12/1998 | Uber, III | 604/151 |
| 5,873,861 A * | 2/1999 | Hitchins et al. | 604/218 |
| 5,885,216 A * | 3/1999 | Evans et al. | 600/431 |
| 5,920,054 A * | 7/1999 | Uber, III | 235/375 |
| 5,947,935 A * | 9/1999 | Rhinehart et al. | 604/218 |
| RE36,648 E * | 4/2000 | Uber et al. | 600/432 |
| 6,096,011 A * | 8/2000 | Trombley et al. | 604/256 |
| 6,099,502 A * | 8/2000 | Duchon et al. | 604/131 |
| 6,149,627 A * | 11/2000 | Uber, III | 604/151 |
| 6,197,000 B1 * | 3/2001 | Reilly et al. | 604/152 |
| 6,221,045 B1 * | 4/2001 | Duchon et al. | 604/151 |
| 6,306,117 B1 * | 10/2001 | Uber, III | 604/151 |
| 6,317,623 B1 * | 11/2001 | Griffiths et al. | 600/431 |
| 6,339,718 B1 * | 1/2002 | Zatezalo et al. | 600/432 |
| RE37,602 E * | 3/2002 | Uber et al. | 600/432 |
| 6,385,483 B1 * | 5/2002 | Uber et al. | 600/431 |
| 6,397,098 B1 * | 5/2002 | Uber et al. | 600/431 |
| 6,402,717 B1 * | 6/2002 | Reilly et al. | 604/67 |
| 6,440,107 B1 * | 8/2002 | Trombley et al. | 604/256 |
| 6,442,418 B1 * | 8/2002 | Evans et al. | 600/431 |
| 6,471,674 B1 * | 10/2002 | Emig et al. | 604/131 |
| 6,475,192 B1 * | 11/2002 | Reilly et al. | 604/189 |
| 6,520,930 B2 * | 2/2003 | Critchlow et al. | 604/67 |
| 6,626,862 B1 | 9/2003 | Duchon et al. | |
| 6,643,537 B1 * | 11/2003 | Zatezalo et al. | 600/432 |
| 6,652,489 B2 * | 11/2003 | Cowan et al. | 604/154 |
| 6,673,033 B1 * | 1/2004 | Sciulli et al. | 604/67 |
| 6,699,219 B2 * | 3/2004 | Emig et al. | 604/131 |
| 6,731,971 B2 * | 5/2004 | Evans et al. | 600/431 |
| 6,733,477 B2 * | 5/2004 | Cowan et al. | 604/181 |
| 6,743,202 B2 * | 6/2004 | Hirschman et al. | 604/131 |
| 6,889,074 B2 * | 5/2005 | Uber et al. | 600/431 |
| 6,901,283 B2 * | 5/2005 | Evans et al. | 600/431 |
| 6,939,302 B2 * | 9/2005 | Griffiths et al. | 600/458 |
| 2002/0143294 A1 * | 10/2002 | Duchon et al. | 604/131 |
| 2007/0197963 A1 * | 8/2007 | Griffiths et al. | 604/97.01 |
| 2007/0213656 A1 * | 9/2007 | Ferdinand | 604/65 |
| 2009/0312740 A1 * | 12/2009 | Kim et al. | 604/500 |

FOREIGN PATENT DOCUMENTS

| | | |
|---|---|---|
| EP | 0581708 A2 | 2/1994 |
| WO | 99/21600 A2 | 5/1999 |

* cited by examiner

CATHETER FLUID CONTROL SYSTEM

CROSS REFERENCE TO RELATED APPLICATIONS

This application is a divisional application of application Ser. No. 10/076,895, filed Feb. 14, 2002, and also claims priority to provisional application Ser. No. 60/268,568, entitled MEDICAL DEVICE WITH AUTO START-UP, filed Feb. 14, 2001, and to provisional application Ser. No. 60/269,112, entitled AUTOMATED BALLOON INFLATION DEVICE USED IN CONJUNCTION WITH AN AUTOMATED VARIABLE DISPENSING RATE INJECTION SYSTEM, filed Feb. 15, 2001, the contents of which are incorporated by reference in their respective entireties.

BACKGROUND OF THE INVENTION

The device pertains to a disposable tubing kit that is attachable to a syringe of an automatic injection device. Automatic injection devices, such as applicants' device described in U.S. Pat. No. 6,099,502 and incorporated by reference herein, are used to deliver fluids such as saline and contrast agents through a catheter to a patient. The devices typically include a motor-driven linear actuator that forces a plunger through a syringe, thereby creating a desired fluid flow into the patient. For sanitation purposes, the syringe and all associated tubing between the patient and the syringe are disposable.

Preparing the automatic injection device for operation is a time-consuming process. Various tubes must be connected together and to the device. The operator preparing the injection device for operation must be careful to ensure that the connections are tight and that none of the tubes are pinched or otherwise blocked. Furthermore, during the assembly process, the operator will prime various subassemblies with saline and contrast before connecting them to other subassemblies. Priming is done to prevent air from being introduced into the patient. Intermittent priming steps are performed so that fluid-to-fluid connections may be made at predetermined assembly steps. For purposes of this discussion, a fluid-to-fluid connection between two components is made by priming each component so that menisci form at their open ends. The ends are then connected together, thereby merging the menisci and ensuring no air is introduced into the connection.

Priming the subassemblies is performed by injecting a desired fluid into the subassembly until the fluid exits the opposite end. The exiting fluid is usually directed into a waste pan, but occasionally spills onto the floor, creating a potential slip hazard, or onto the patient, who is awake during most of the procedures involving the automatic injection device. In addition to creating slip hazards or causing discomfort to the patient, there is growing interest in minimizing the presence of open fluid containers in medical environments. This is especially true for bodily fluids, such as blood, which present a potential biohazard.

Once assembled, the components are again primed with fluid to prevent air from being injected into the patient. While priming, the operator taps on the various components in an attempt to dislodge air bubbles from their inner walls. The entire set-up process typically takes 10 to 15 minutes and requires a trained operator. Opportunity for error exists even when the set-up is carefully performed by a trained operator.

Some completely assembled, disposable kits are available that include a syringe that is pre-loaded with contrast agent. These kits overcome some of the aforementioned difficulties but present their own challenges to the manufacturer. All medical devices must be delivered sterile and are thus sterilized prior to shipping. Present methods of sterilization include heating using wet or dry autoclaving, gamma irradiation, or EtO sterilization. Each method has drawbacks. Dry autoclaving requires very high temperatures to overcome the lack of heat transfer inherent in dry systems. Wet or steam autoclaving causes dimensional increases in plastic components as the moisture penetrates the plastic and a subsequent decrease as the moisture later escapes. Steam autoclaving further uses a temperature which may cause the polymeric parts to deform. Gamma irradiation requires the use of gamma-stable components and, further, degrades contrast agents, and EtO requires a subsequent out-gassing step to remove byproducts of the sterilization process, and is also expensive, inflexible and difficult to verify or control.

Regardless of whether the syringe is pre-filled, once the set-up is complete, the physician positions a catheter into the patient. The use and type of the catheter varies depending on the procedure being performed. For example, the catheter may be used to deliver contrast agents, using the aforementioned injection device, or to provide a guide for routing bioptomes, ultrasonic imaging probes, or balloon devices.

Some of the devices require fluid flow, such as the balloon devices, and are connected to special manual syringes. These special syringes are called "inflators" and use a plunger that is manually advanced using a rod that is threaded into a handle to allow the operator to advance the plunger using very small, controlled increments. However, these threads also give the physician such a mechanical advantage as to take away the "feel" of the balloon inflation. Thus, the physician cannot feel the effect the balloon is having on the wall of the vessel it is stretching. For example, the physician cannot feel a calcium deposit cracking. The special syringes typically include a pressure gauge but it is located on the syringe itself and is impractical for the physician to monitor the gauge as he or she is often watching an image of the balloon being inflated on a monitor. It would be advantageous to use the automatic injection device to accomplish controlled injections of fluid for purposes such as inflating balloons so that a greater degree of inflation accuracy and control is achieved and so a more precise and accurate feedback loop is attained. However, automatic injection devices are generally constructed and arranged to accommodate a large-capacity syringe such as the syringe used to inject contrast agent. This type of syringe is too large to be used for balloon inflation because the injection device cannot move the linear actuator over a short enough distance and with the necessary precision and accuracy for a balloon inflation procedure. Additionally, the larger syringe exhibits greater compliance. To provide the necessary accuracy, a smaller syringe would have to be used so that a given linear distance traveled by the actuator results in a much smaller volume of liquid being injected. However, a small syringe, such as the manual syringe used to inflate a balloon, is not compatible with the present automatic injection devices.

There is a need for a device and method for reducing the set-up time associated with using an automatic injection device.

There is also a need for a device that minimizes the chances of error by an operator in setting up an automatic injection machine for use.

There is a further need for a device and method that improves management of waste while performing catheter-based surgical procedures.

There is thus a need for an adapter that would allow the automatic injection device to be used to inject small, precisely measured and controlled amounts of fluid.

BRIEF SUMMARY OF THE INVENTION

The present invention includes a method and device for inflating a balloon using an automatic inflation device. The device for inflating a balloon includes a significantly smaller syringe than that typically used in the automatic inflation device. The smaller syringe provides increased control over the administration of a small quantity of fluid. An adapter sleeve is provided that is attachable to an automatic injector device to provide support for the smaller syringe. Present automatic injection devices, such as the CL100 designed by Acist Medical Systems, Inc. of Eden Prairie, Minn., are designed for large volume injections of contrast media. These devices are designed to accept large syringes. The adapter sleeve, thus, has an outside diameter or dimension substantially equal to that of a syringe used in the device for contrast agents, and an interior diameter or dimension substantially equal to that of the balloon syringe.

The automatic injector is programmed to provide a balloon inflation mode of operation. Once the sleeve and balloon inflation syringe are installed, the device may be used to automatically fill the syringe with contrast agent or saline. The device may be placed in inflation mode manually, or it may be constructed and arranged to automatically detect the presence of the adapter sleeve and place itself into inflation mode accordingly. Preferably the linear actuator and motor of the automatic injector are used to act on the plunger or "wiper" of the balloon inflation syringe. Alternatively, an adapter may be provided including an auxiliary linear actuator device driven by a linear stepper motor, hydraulic cylinder, piezoelectric inch-worm handheld actuator, or the like.

In addition to a physiologic pressure transducer, which provides a pressure input to the monitor for display or other purposes that is representative of biological pressures, one aspect of the invention is a pressure sensor for measuring a pressure representative of the pressure in the balloon. Balloon pressures are significantly higher than biologic pressures. To avoid damaging the sensitive physiologic pressure transducer, the present invention provides a pressure sensor that is separate from the physiologic pressure transducer. This sensor may be a separate pressure transducer, capable of higher pressures. Or it may be an indirect sensor, such as a motor torque detector, which provides a value, representative of motor torque, that can be converted to balloon pressure. Alternatively, strain gauges may be operatively attached to the housing structure surrounding the syringe to measure the axial load on the housing, which is representative of the pressure exerted by the fluid inside the syringe.

Another aspect of the invention provides a fluid detection feature. This is a safety feature that insures against air being injected into the patient. This feature may be embodied in a passive coating on the interior surface of the syringe or tubing that reacts when contacted by a fluid. This feature may also be embodied by an active device using ultrasound, optics, or conductivity to determine the presence or absence of fluid in the syringe.

The method of using the device to inflate a balloon begins by setting the device to the balloon inflation mode. Again, this preferably occurs automatically when the computer of the automatic inflation device receives a signal from a sensor that is constructed and arranged to detect the presence of the adapter sleeve. The adapter and syringe are then loaded onto the device. Next the balloon catheter is attached and all air is aspirated therefrom and expelled from the system. The balloon and associated tubing are then preloaded with either contrast agent or saline and primed.

The balloon and automatic inflation device having thus been prepared, the balloon is inserted into the patient and positioned at the target site. The desired parameters are programmed into the device and inflation is initiated. One aspect of the present invention is that the desired parameters may be calculated automatically based upon inputted data such as patient weight, percent occlusion of the target vessel, type of balloon, etc. Further, the balloon inflation device may perform a small test inflation to determine the elasticity of the artery or vein from which the actual program function is determined.

While the balloon is inflating, the inflation speed may either be preprogrammed and allowed to inflate in a fully automatic mode, or controlled from outside or within the sterile field with remote devices such as a handheld device or using a touch screen, in data flow communication with the computer, that is preferably covered with a transparent drape. The balloon pressure, balloon volume, and inflation time are outputted to a display screen. The pressure and volume are preferably also displayed as a graph as a function of time. The balloon pressure and volume are monitored for dilatation. A sudden increase in volume or a sudden decrease in pressure can indicate that a buildup of calcium in a blood vessel has cracked or "popped", a desired result of balloon therapy for arteriosclerosis. This sudden spike in volume is followed by a subsequent pressure increase indicating a momentary or incremental pressure drop. If the pressure falls below a preset limit, corrected for volume, or is not regained by further inflation, the sudden pressure drop may be indicative that the balloon has ruptured. If it is determined that the balloon has ruptured, the procedure is stopped or reversed automatically or by depressing a stop button on the device.

One aspect of the invention provides an automatic detection program that enables the computer controlling the automatic injection device to recognize the occurrence of a "pop" and to stop inflating thereafter, either by deflating the balloon (drawing back on the plunger—aspirating), by holding the balloon pressure constant for a predetermined time (moving the plunger forward under pressure control) or by providing keep-open flow (moving the plunger forward under flow control) or by simply halting motion of the plunger in either direction. This safety feature prevents the possibility of over-inflating the balloon, and thus stressing the blood vessel. The feature can also minimize the unnecessary introduction of fluid into the blood vessel in the event of a balloon rupture.

Another aspect of the present invention provides an automatic detection program that measures the actual pressure in the balloon catheter, and the volume of fluid injected, and compares that data to baseline pressure data representative of inflation characteristics of the balloon catheter in controlled environment. The difference between actual data and baseline pressure data represents the effect of the patient on the balloon catheter. This information can be used to determine the effectiveness of the balloon catheter and may also be used to trigger certain actions by the computer. Such actions might include a shut down or aspiration if the data seems to indicate that there is a safety issue, such as a balloon rupture. Another action might be to hold the balloon pressure at a predetermined level for a period of time after a pop has been detected. Another action might be to follow a pressure versus time algorithm previously inputted into the computer. Yet another action executable by the computer is to control the balloon volume, regardless of, or in addition to, balloon pressure.

The baseline pressure data will be different for various balloon catheters and is preferably provided in the form of a bar code or other form of computer readable data on or in the package of the balloon catheter. The automatic injection device includes a bar code reader or other correlative device usable to retrieve the baseline pressure data from the package. The computer can also be used to record the balloon pressure as a function of time or volume, baseline pressure as a function of time or volume, injection rate as a function of time, and any other data that the computer may be programmed to use or record so that each procedure, or case, can be recorded as a computer file and used later for analysis or as a record to be inserted into the patient's file.

One embodiment provides the capability to create and display three-dimensional graphs that are easily readable by the physician. The third dimension may take the form of a conventional plane—style graph, i.e. a graph having x, y, and z axes. Alternatively a two dimensional plot may be provided using colors or audible tones to provide the third dimension. Example of three dimensional data sets include pressure, volume, and time; pressure, volume, and radiographic balloon opacity; pressure, volume and balloon diameter; and the like.

Once the balloon treatment is complete, the balloon is deflated and the catheter is removed from the patient. The device may be stopped or it may be placed in a standby mode and used on another patient. The automatic detection program may include an automatic deflate mode whereby the movement of the syringe plunger is automatically reversed when the "pop" is detected, until it is determined the balloon is deflated. The pressure sensor may be used to determine whether the balloon is deflated.

The automatic inflation device, combined with the automatic detection program, makes it possible to inflate multiple balloons simultaneously. By automating the procedure, the physician is free to concentrate on the device monitors and is thus able oversee multiple balloons. The automatic inflation device is further capable of being programmed in a phased manner such that the inflation of various balloons can happen either simultaneously or sequentially.

DETAILED DESCRIPTION OF THE INVENTION

Figure 1:
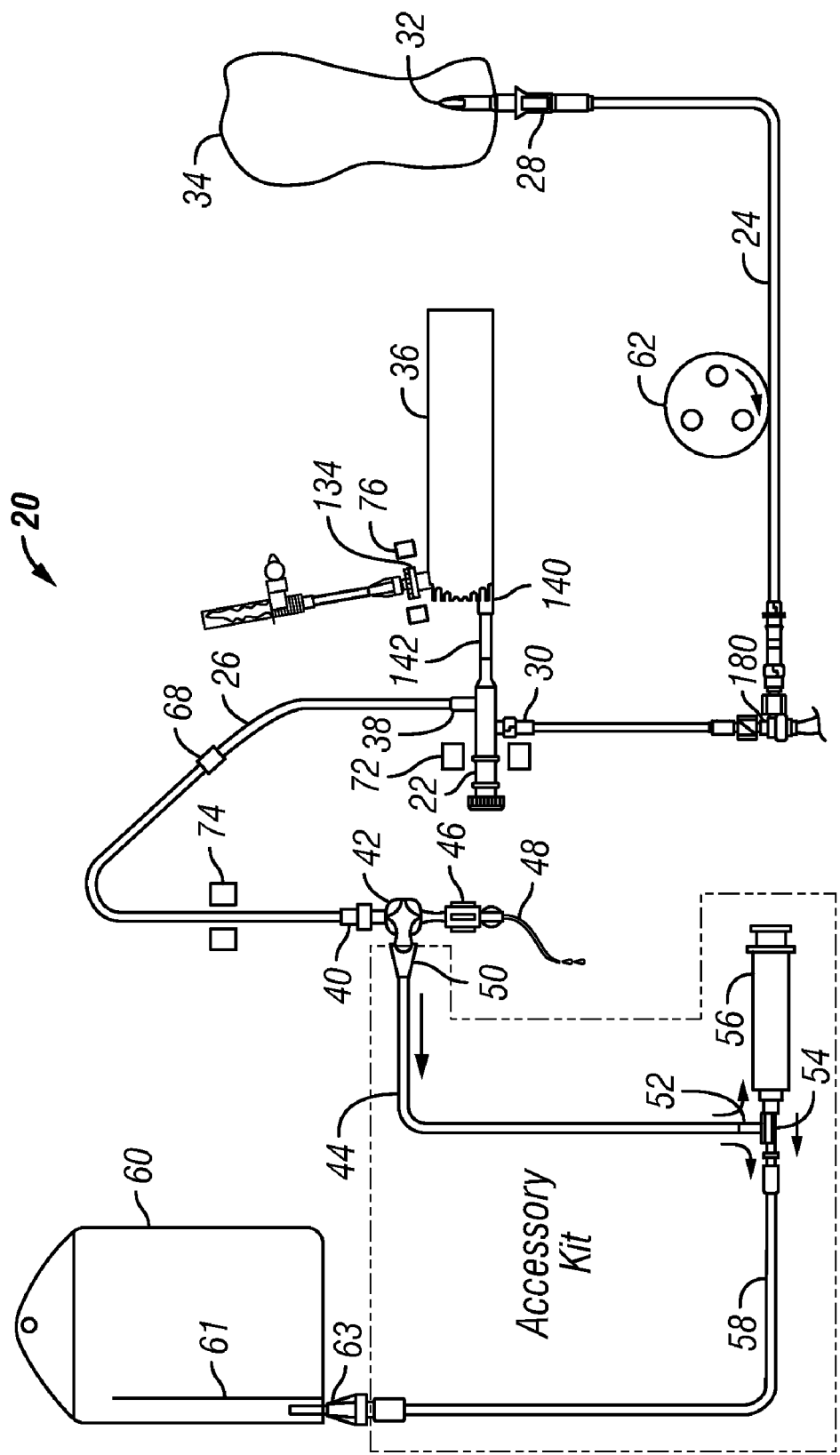
FIG. 1 is a diagrammatic representation of an embodiment of the fluid network of the present invention.

Referring now to the Figures, and first to FIG. 1, there is shown a fluid network 20 comprising a disposable patient manifold 22 connected to a saline line 24 and an output line 26. The saline line 24 has a first end 28 and a second end 30. The first end 26 is connected to a bag connector 32, useable to establish fluid communication between the line 24 and a saline bag 34.

The patient manifold 22 is also connected to a syringe 36 of an automatic injection device (not shown) for receiving the fluid ejected therefrom. The patient manifold 22 is thus useable to selectably connect the output line 26 with either the saline line 24 or the syringe 36. The patient manifold 22 may be any device capable of selectively directing flow between at least three ports, such as a three-way check valve, a manual or automatic three-way stopcock, a motor operated valve, or a collection of check valves operably disposed within the appropriate lines to effect the desired flow directions. Preferably, the patient manifold 22 comprises an automatic valve that is constructed and arranged such that fluid communication normally exists between the saline line 24 and the output line 26. However, when a predetermined amount of positive fluid pressure is generated by the syringe 36, the fluid pressure causes the fluid communication between the saline line 24 and the output line 26 to become blocked, and opens fluid communication between the syringe 36 and the output line 26. An example of this type of patient manifold is the spring-loaded spool valve described in U.S. patent application Ser. No. 09/542,422, incorporated by reference herein in its entirety. To provide controlled saline pressure when the patient manifold 22 is aligned to deliver saline to the output line 26, the saline line 24 is fed through a pump, preferably a peristaltic pump 62, of the automatic injection device.

The output line 26 is connected at a first end 38 to the patient manifold 22 and at a second end 40 to a three-way stopcock 42. The three-way stopcock 42 may be manually or automatically operated and is also connected to a waste line 44 and a catheter connector 46 such that it may be used to align the output line 26 with either a catheter 48 or the waste line 44.

The waste line 44 has a first end 50 connected to the three-way stopcock 42 and a second end 52 connected to a three-way check valve 54. The three-way check valve 54 is also connected to an auxiliary syringe 56 and a bag line 58. The three-way check valve 54 is constructed and arranged so that the auxiliary syringe 56 may be used as a hand pump. When the wiper of the syringe 56 is withdrawn, the check valve 54 blocks the bag line 58 and directs fluid from the waste line 44 into the syringe 56. When the wiper is then advanced, the check valve 54 blocks the waste line 44 and directs fluid from the syringe 56 into the bag line 58. The bag line 58 is connected to a waste bag 60 where the waste fluid is deposited. When the syringe 56 is used to aspirate saline into the waste bag 60, it is important that the saline line 24 is not compressed and occluded by the peristaltic pump 62.

Figure 2:
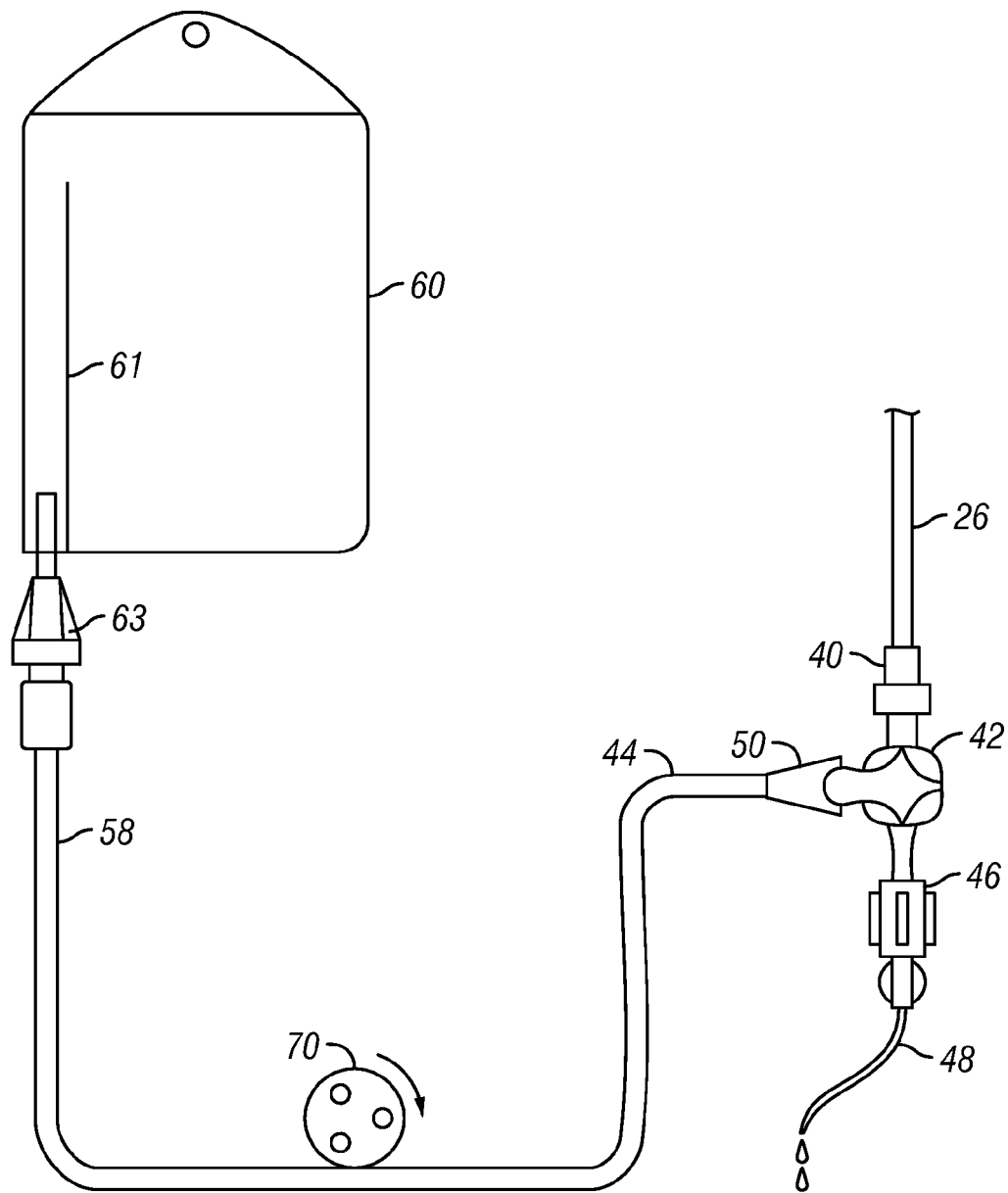
FIG. 2 is a diagrammatic representation of an alternative embodiment of the fluid network of the present invention.

Alternatively, as seen in FIG. 2, an automatic pump 70 may be used to pump liquid to the waste bag 60. The automatic pump 70 is shown as a peristaltic pump that acts on the waste line 44. As peristaltic pumps act on the outside of a tube, the waste line 44 and the bag line 58 are integral.

The fluid network 20 is thus designed to be attached to an automatic injection device quickly and primed with little or no human interaction. The fluid network 20 is assembled, packaged and sterilized so that it may be shipped as a completely assembled kit. Preferably, the waste bag 60 doubles in function as the packaging bag in which all of the aforementioned components of the fluid communication network 20 are shipped. This eliminates the need for a separate packaging bag, an added expense. A divider 61 is integrated, preferably by heat sealing, into the bag to limit the amount of fluid that could spill from the bag 60 in the event of a leak developing around the connection 63 between the bag 60 and the bag line 58.

In use, the fluid network 20 is removed from its packaging and the patient manifold 22 is connected to the syringe of the automatic injection device. The saline line 24 is threaded through the peristaltic pump 62 and verification is made that the three-way stopcock 42 is aligned to the waste line 44. Next, the bag line 58 is connected to the waste bag 60 and the saline line 24 is connected to the saline bag 34.

The fluid network 20 is now ready for priming. The automatic injection device, such as the device 102 shown in FIG. 3 and discussed in more detail below, preferably includes a computer 106 having a program segment for instructing the device 102 to enter a priming mode. When selected, the priming mode program segment includes a command that causes the computer 106 to align the patient manifold 22 for contrast agent, or if the patient manifold 22 is a manually operated valve, displays a message instructing the operator to do so. The program segment prevents further action unless the computer 106 receives verification from the operator that the manifold 22 is aligned. Preferably, a patient manifold position detector 72 is operably connected to the manifold 22 and in communication with the computer 106, obviating the need for verification from the operator. Once the position of the manifold 22 is verified, either by operator input or with the detector 72, the program segment causes the computer 106 to send a signal to the linear actuator of the automatic injector that advances the plunger of the syringe 36 slightly to force potential air bubbles from the syringe connecting tube 66, which connects the patient manifold 22 to the syringe 36. Any air bubbles in the connecting tube 66 are forced into the output line 26.

The priming program segment 64 then aligns the patient manifold 22 for saline. After manifold position detector 72 verifies that the patient manifold 22 is aligned for saline, the peristaltic pump 62 is activated for a predetermined interval. The interval is long enough, for a given pump speed, to fill the saline line 24, the patient manifold 22 and the output line 26 with saline.

Preferably, the peristaltic pump 62 operates in a priming mode whereby it turns in a stutter fashion to send pressure pulses through the various lines. These pressure pulses act to dislodge air bubbles from the inner walls of the lines, thus obviating the need for the operator to tap on the lines during the priming procedure. To monitor for the presence of bubbles, a bubble detector 74 is placed in one or more locations and are electrically connected to the computer of the automatic injector. In priming mode, detection of bubbles is expected. However, when the injector is in injection mode, the receipt of a signal from the bubble detector(s) 74 will cause the injector to stop forward movement of the plunger of the syringe 36. The waste bag 60 eventually receives all of the priming fluid.

Alternatively, if a syringe pump (not shown) is used instead of a peristaltic pump 62, the syringe may be operated by a linear actuator in a stutter fashion such that the linear actuator intermittently hammers on the plunger of the syringe thereby creating the necessary pressure pulses to dislodge air bubbles from the inner walls of the various lines. One skilled in the art will see that any pump substituted for the peristaltic pump 62 can be operated in an on and off fashion to create such pressure pulses.

Priming having thus been completed, the attending physician may insert the catheter 48 into the target blood vessel and attach the catheter 48 to the fluid communication network 20 using the catheter connector 46. The catheter 48 is then primed, and proper placement within the vessel is verified, by taking a suction on the catheter 48 until blood appears in the clear tubing of the output line 26. Taking suction on the catheter 48 is performed by aligning the stopcock 42 to establish fluid communication between the output line 26 and the catheter 48. Suction may then be drawn on the output line 26 by retracting the plunger of the syringe 36, or reversing the rotation of the peristaltic pump 62. However, it may be undesirable to establish reverse fluid flow into the syringe 36 or the saline bag 32. Doing so prevents reuse of the saline remaining in the saline bag 34 and reuse of the contrast agent in the syringe 36. More preferably, the output line 26 includes a disconnect 68 that allows the physician to connect a hand syringe to the output line 26 and take a suction thereon. Once blood appears in the clear output line 26, the disconnect 68 is reconnected and the three-way stopcock 42 is aligned to the waste line 44. The peristaltic pump 62 is then run in a forward direction to force the blood from the output line 26, through the stopcock 42, and into the waste line 44. The waste bag 60 receives the blood and other waste fluids for safe containment and easy disposal.

Figure 3:
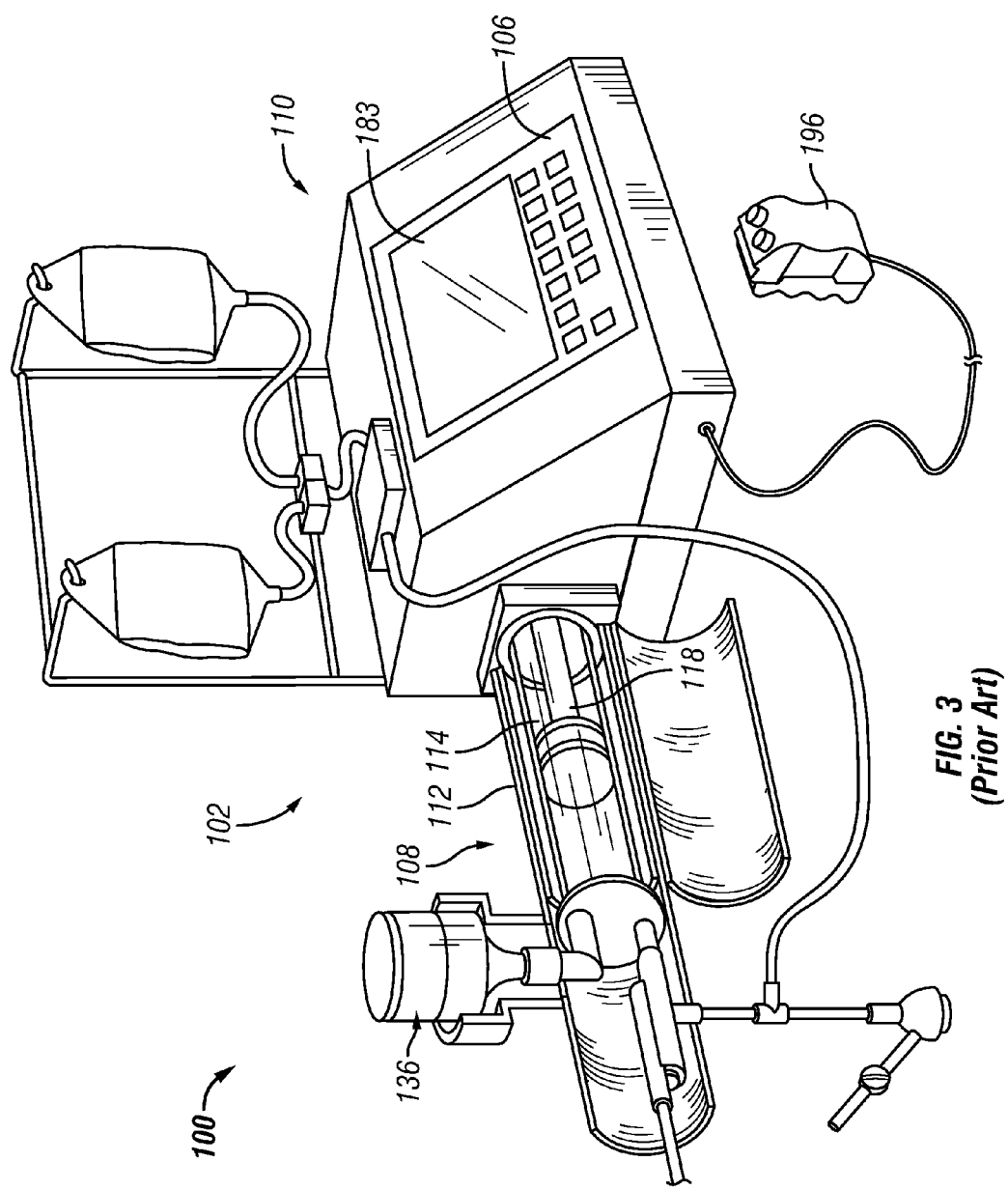
FIG. 3 is a perspective view of a prior art automatic injector device that is convertible to a balloon inflation device of the present invention.
Figures 3A, 3B:
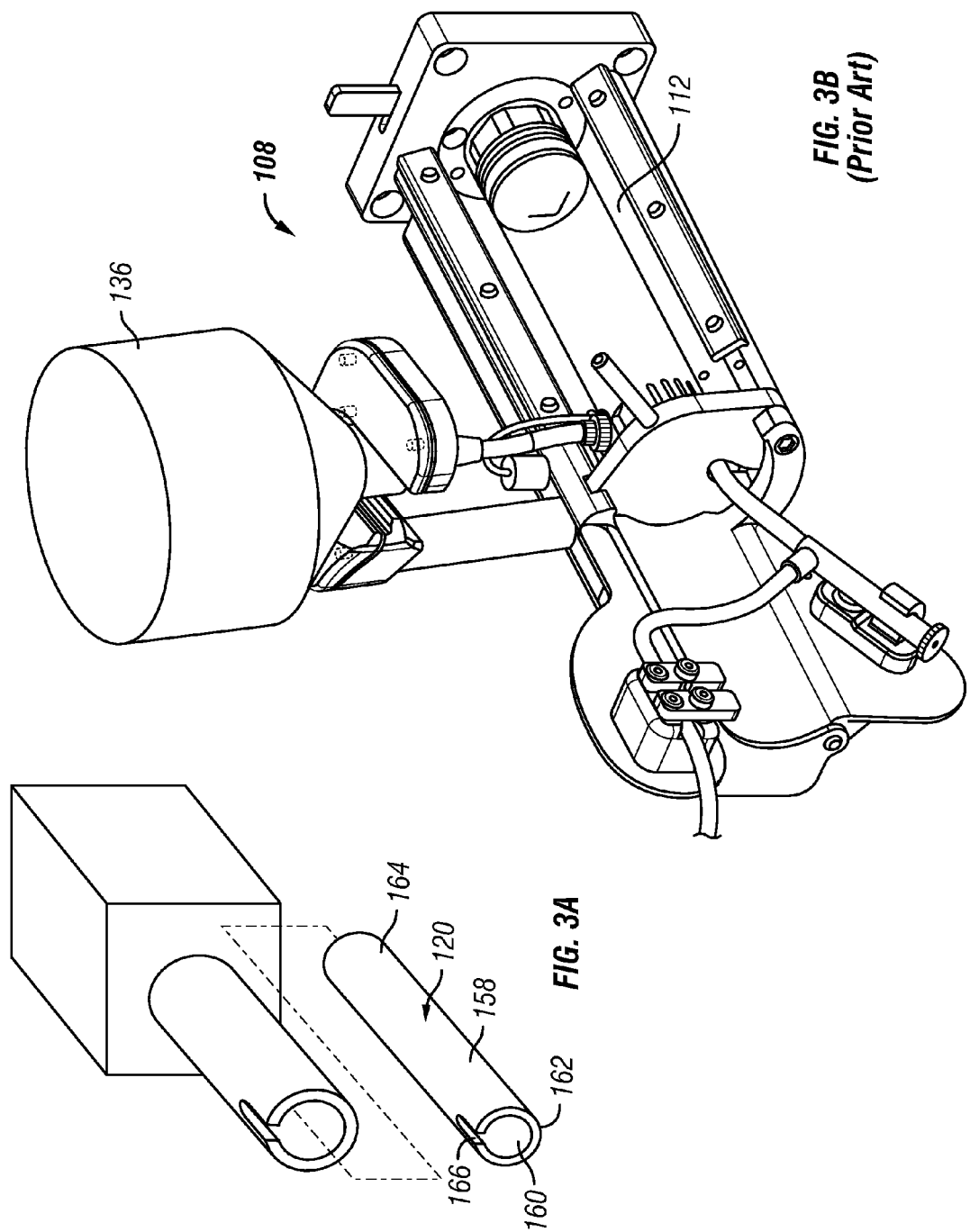
FIG. 3A is a perspective view of an adapter sleeve, useable to convert an automatic injector device into a balloon inflation device of the present invention.
FIG. 3B is a perspective view of a prior art injector subassembly of an automatic injection device.

Referring now to FIGS. 3, 3A, and 3B, another embodiment of the present invention provides an automatic balloon inflation device 100. This embodiment of the balloon inflation device 100 is constructed and arranged to allow an existing automatic injection device 102, such as the CL100 made by Acist Medical Systems, Inc. of Eden Prairie, Minn. and described in U.S. Pat. No. 6,099,502 incorporated by reference herein in its entirety. It is understood by one skilled in the art that a separate balloon inflation device could be constructed using the devices and techniques represented herein combined with the necessarily associated functionality of existing angiographic injectors.

The automatic injection device 102 is converted into a balloon inflation device 100, when it is accessorized to accept a small, balloon inflation syringe 104 (FIGS. 6 and 7), and when the computer 106 of the injection device 102, is updated with a program that allows the injection device 102 to operate in "Inflation Mode".

Figure 4:
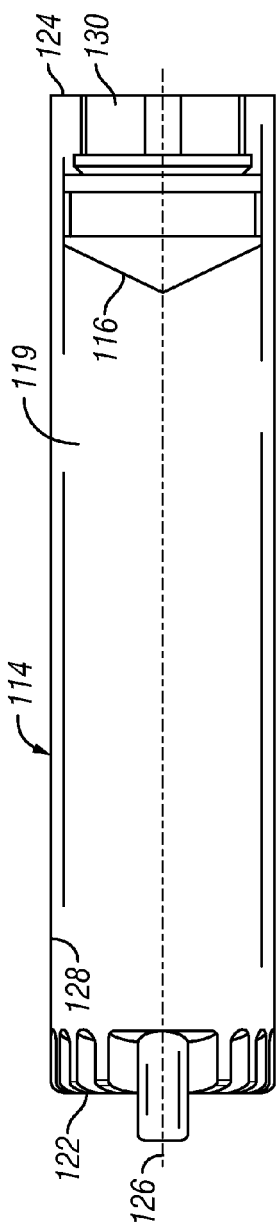
FIG. 4 is bottom view of a prior art syringe insertable into an injector device.
Figure 5:
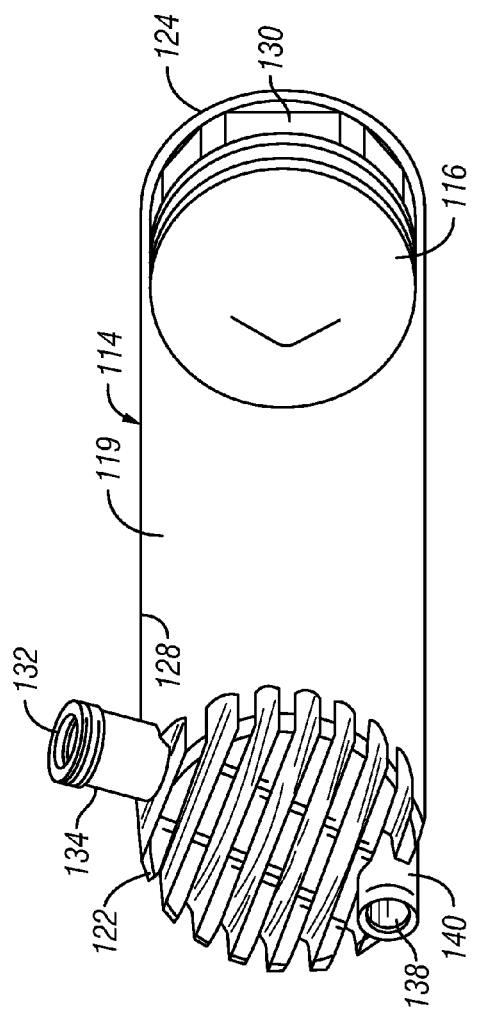
FIG. 5 is a perspective view of the prior art syringe of FIG. 4.

The example of an automatic injection device 102 shown in FIG. 3 includes an injector subassembly 108 and a user-interface subassembly 110. The injector subassembly 108 includes a syringe holder 112, typically used to house a relatively large syringe body 114 having fluid capacities on the order of 10 cc to 250 cc, such as those used for angiography and shown in FIGS. 4 and 5. The syringe body 114 is equipped with a plunger 116, slideably disposed therein. The plunger is acted upon by a linear actuator 118 (FIG. 3) of the injector subassembly and is removably attached thereto. The particular angiography syringe body 114 shown in FIGS. 4 and 5, is fully described in U.S. Pat. No. 6,099,502 and includes features that an automatic injection device, the injector subassembly of which is shown in FIG. 3B. These features are discussed briefly herein as they provide examples of injector-specific considerations that are made in the design of a conversion kit to allow the injector 102 to be used as a balloon injector 100. These features may also be incorporated into the design of a balloon inflation syringe 104.

Thus, the angiography syringe 114 includes a wall 119 defining first and second opposite ends 122, and 124. The first end 122 corresponds to a distal end of the syringe 114, and the second end 124 corresponds to a proximal end of the syringe 114. The wall 119 of the syringe 114 is cylindrical in the illustrated embodiment and includes a central axis 126 extending longitudinally therethrough.

The syringe body 114 defines a pumping chamber 128 in an interior thereof. A wiper or plunger 116 is located in the pumping chamber 128 and is constructed and arranged for reciprocal motion between a position adjacent to the first end 122 and the second end 124. That is, when the syringe 114 is mounted in a system analogous to the angiographic system 102, the linear actuator 118 from the system energizes the plunger 116 and causes it to move between the second end 124 and the first end 122. A plunger support member 130 supports the plunger 116. The support member 130 preferably comprises a rigid, hard material for example, a polycarbonate or ABS plastic, to interface between an actuator 118 and the plunger 116. The member 130 attaches to the plunger 116 by a snap fit, a magnetic fit, or a similar quick attach coupling that allows the plunger 116 to be pushed and pulled.

The syringe 114 defines at least one port for providing fluid flow communication with the pumping chamber 128. In the particular embodiment illustrated, the syringe 114 includes two ports providing fluid flow communication with the pumping chamber 128. Specifically, an inlet port 132 allows the pumping chamber 128 in the syringe 114 to be filled with contrast material, and purged of air through the inlet port 132. A housing 134 circumscribes the inlet port 132 and allows the inlet port 132 to be connected with an appropriate bottle or bag 136 (FIGS. 3 and 3B) of contrast agent or saline. When the syringe 114 is oriented in a syringe holder 112 in an angiographic system as described above, the inlet port 132 is located above the pumping chamber 128.

The inlet port housing 134 is preferably clear because one aspect of the present invention provides a fluid detection device 76 (FIG. 1) that is preferably operably connected to the housing 134. The device ensures that all air has been purged from the syringe 114 and that fluid occupies the housing 134. The fluid detection device may be embodied in a passive coating on the interior surface of the syringe that reacts when contacted by a fluid. Alternatively, the device may be embodied using an ultrasound, optic, or electromagnetic emitter to detect the presence of fluid in the housing 134. One embodiment provides an optic sensor used to determine the position of a floating ball of a floating ball valve. When the ball is supported by fluid in an up position, any air in the syringe 114 has been purged. Though the syringe 114 shown in FIGS. 4 and 5 is denoted as prior art, as mentioned above, the fluid detection device 76 is considered a novel aspect of the present invention.

In this embodiment, the syringe 114 is mounted in an angiographic system at an angle such that any air bubbles present in the pumping chamber 128 migrate toward the inlet port 132, through which they may be purged. To purge air through the inlet port 132, the inlet port housing 134 houses a valve assembly that permits air to be expelled or purged from the syringe 114, but does not allow fluid to flow out of the pumping chamber 128 and back into the bottle 136 of contrast fluid when pressure movement is applied on the syringe side of the check valve. Such a check valve is described in U.S. Pat. No. 6,099,502.

The syringe 114 also includes an outlet port 138 in fluid flow communication with the pumping chamber 128. The outlet port 138 permits fluid flow from the pumping chamber 128 to a fluid communication network, such as fluid network 20. The outlet port 138 is surrounded, or circumscribed, by an outlet port housing 140 extending, or projecting, from the end wall of the syringe 114. The outlet port housing 140 is constructed and arranged to receive a patient manifold connector tube 142 (FIG. 1).

The syringe body 114 is too large for use as a balloon inflation syringe. However, the syringe holder 112 is constructed and arranged specifically to hold a particular syringe body 114. Thus, to place a balloon inflation syringe in the syringe holder and provide proper alignment with relation to the linear actuator 118, and provide the necessary support needed to operate a relatively thin-walled balloon inflation syringe with a powerful linear actuator 118, the present invention provides an adapter sleeve 120, shown in FIG. 3A and in phantom in FIG. 6, constructed and arranged with outer dimensions that allow the sleeve 120 to be properly cradled by the syringe holder 112. The inside cavity of the adapter sleeve is configured to closely mate with a balloon inflation syringe 104.

The balloon inflation syringe 104 is preferably closely analogous to the angiographic syringe 114, to allow attachment of the balloon inflation syringe 104 to the injector subassembly 108. Thus, the balloon inflation syringe 104 includes a wall that defines a pumping chamber 146 therein that is an appropriately small size to allow controlled balloon inflation, typically on the order of 5 ml to 40 ml. The syringe 104 also includes a plunger 148 that attaches to the linear actuator 118 in the same manner as the plunger 116 of the syringe 114. An inlet port 150, defined by an inlet port housing 152, establishes fluid communication between the supply bottle 136 and the pumping chamber 146. The inlet port housing 152 is longer than the analogous inlet port housing 134 of the angiographic syringe 114 to allow for the smaller diameter of the balloon inflation syringe 104. An outlet port 154 defined by an outlet port housing 156, establishes fluid communication between the patient manifold connector 142 and the pumping chamber 146 of the balloon inflation syringe 104.

Similar to the ports 132 and 138 of the angiographic syringe 114, described above, the inlet port 150 and the outlet port 154 of the balloon inflation syringe 104 are located in upper portions and lower portions of the syringe 104 when the syringe 104 is loaded into the injector device 100. However, as much less fluid is being injected, and it is very rare to inject all of the fluid located in the pumping chamber 146 during a balloon inflation procedure, there may be less importance placed on the location of the ports 150 and 154. For example, the balloon inflation syringe 104 may be supplied pre-loaded with fluid, obviating the need for an inlet port 150. Further, the outlet port 154 may be more conventionally located along a central axis of the syringe 104, so long as the particular injection device 100, to which the adapter sleeve 120 is designed, accommodates the placement of the outlet port 154.

Figure 6:
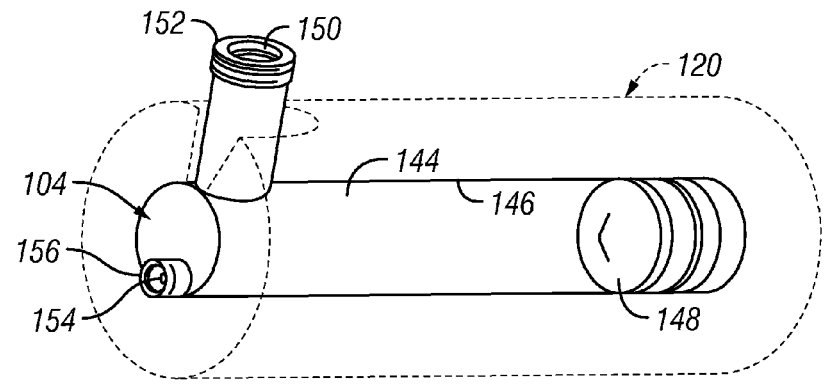
FIG. 6 is a perspective view of a syringe of the present invention surrounded by an adapter sleeve of the present invention shown in phantom lines.

Referring again to FIGS. 3A and 6, the adapter sleeve 120 is described in greater detail. The adapter sleeve 120 has an outer wall 158 defining an inner cavity 160 having an inside diameter substantially equal to the outside diameter of the balloon inflation syringe 104. The outer wall 158 is open at a first end 162 and a second end 164 such that the balloon inflation syringe 104 may be loaded into the first end 162 and so that the linear actuator 118 may act on the plunger 148 of the syringe 104 through the second end 164. The outer wall 158 also defines a groove 166 at the first end 162 that is constructed and arranged to accept the inlet port housing 152. FIG. 6 shows that when the syringe 104 is mated with the sleeve 120, the size and shape of the resulting assembly is substantially the same as the size and shape of the angiographic syringe 114.

Figure 7:
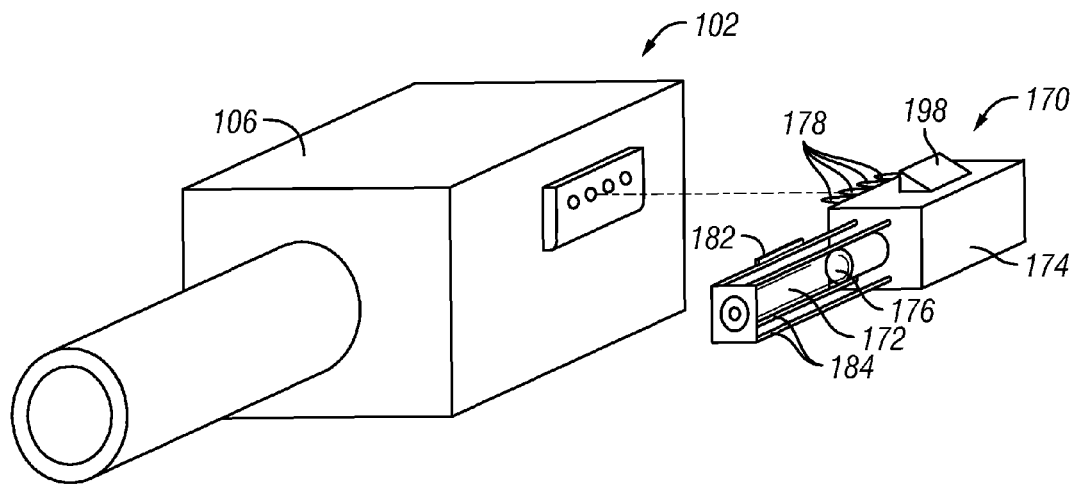
FIG. 7 is an embodiment of a balloon inflation device of the present invention.

FIG. 7 shows an alternative embodiment of a balloon inflation device 170. The balloon inflation device 170 is a self-contained unit that is attachable to an automatic injection device 102. This arrangement obviates the need for switching syringes and inserting adapter sleeves when transitioning from a diagnostic imaging procedure to a balloon catheter procedure. Additionally, providing the balloon inflation device 170 as a self-contained unit allows for the use of common electronics and controls to be used for supplying power and commands to the mechanical components of the device 170.

The balloon inflation device 170 includes an appropriately sized syringe 172 operably attached to a linear actuator module 174. The linear actuator module 174 contains an actuating device, such as a motor or hydraulic or pneumatic piston, useable to move a plunger 176 slideably disposed within the syringe 172.

The linear actuator module is able to receive and respond to commands given by the computer 106 of the automatic inflation device 102, and receive the necessary power to drive the actuating device, through connector pins 178.

An advantage to providing a computer driven balloon inflation device, such as balloon inflation device 100 or 172, is that the device can become integrated into a closed feedback loop that can be used to accurately achieve desired pressures within a balloon catheter during an inflation procedure. Referring back to FIG. 1, there is shown a pressure transducer 180 located within the fluid communication network 20 on the saline line 24. The pressure transducer 180 is a sensitive instrument, capable of measuring small changes in pressure, such as those pertaining to biological patient attributes. Locating the pressure transducer 180 on the saline line 24 allows the patient manifold 22 to be used to insulate the transducer 180 from any high pressures that may be generated by the syringe 36.

A pressure sensor, such as the strain gauge 182, shown in FIG. 7, can be used for high pressures, such as those developed by the balloon inflation syringe 104. The strain gauge 182 is mounted to one of four syringe support rods 184 that are used to fix the syringe 172 to the linear actuator module 174. Balloon pressure may be accurately determined by measuring the amount of strain encountered by the support rods 184 as the plunger 176 is depressed. Alternatively, pressure may be measured as a function of the load placed on the linear actuator module 174. For example, if a DC motor is used to drive the linear actuator of the module 174, a circuit may be incorporated into the electronics driving the motor that is constructed and arranged to measure motor torque as a function of current drawn.

The feedback loop is formed by measuring balloon pressure and providing it to the computer 106, which then uses it to increase or decrease the amount of pressure it instructs the linear actuator module 174 or linear actuator 118 to place on the plunger 176 or 148, respectively. A significant advantage to forming a computerized feedback loop is the ability to load a program segment into the memory of the computer 106 that provides a target map to be used by the computer 106 for calculating error and determining corrective action. Another program segment can be used to create a display of target pressure and actual pressure, either numerically or graphically.

Figure 8:
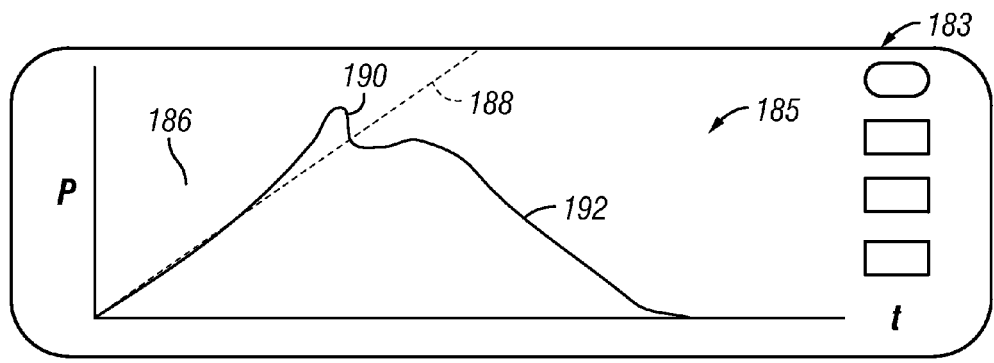
FIGS. 8-10 are examples of pressure graphs shown on a display of the present invention during balloon inflation procedures.
Figure 9:
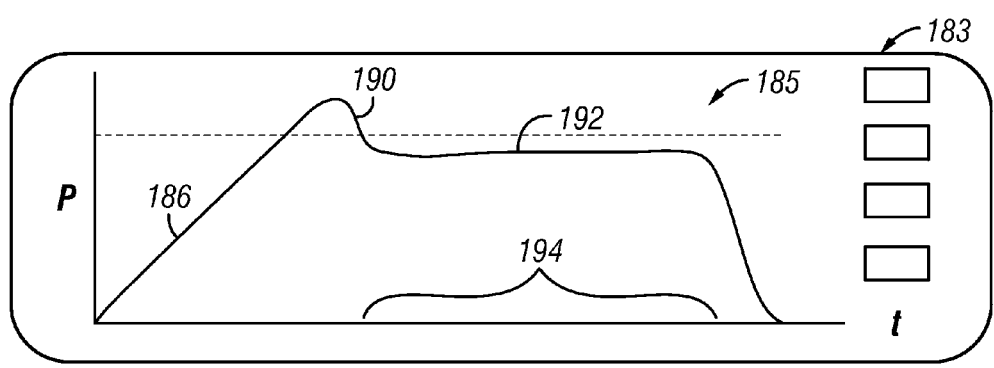
Figure 10:
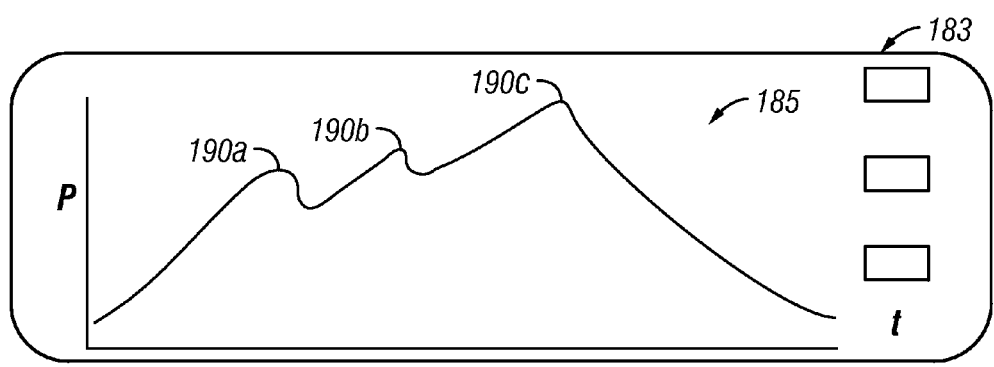

Referring now to FIGS. 8-10, there are provided examples of displays 183 showing pressure versus time graphs 185 (units and values have been omitted but are understood to be included in an actual display). A similar graph may be provided for balloon volume versus time (not shown).

FIG. 8 shows a display 183 with a graph 185 that may represent a typical balloon inflation pressure profile when a balloon is used to dilate an area in a blood vessel that has become restricted due to a build-up of plaque. At 186, the balloon is inflating and pressure is rising steadily as the fluid meets with increasing resistance from the balloon and the walls of the vessel. The dotted line 188 represents the particular inflation characteristics of the balloon catheter being used in the procedure. This will be discussed in more detail below.

Typically during this procedure, there will be a sudden drop in pressure 190. This is known as a "pop" and it represents the plaque buildup giving way, the ultimate goal of the procedure. By breaking the bonds that hold the plaque together, the vessel is allowed to return to a diameter closer to that of its original size. When a balloon is being inflated manually, the physician pays attention to feeling this "pop" in the syringe being used to inflate the balloon. With the feedback loop of the present invention, a program segment is provided that allows the computer 106 to sense this "pop" and take a desired action thereafter. The graph in FIG. 8 shows that the desired action in this case was to deflate the balloon at 192.

FIG. 9 shows a similar graph 185. However, in this case, the desired action after the "pop" at 190 is to hold the pressure in the balloon constant at 192 for a predetermined period of time 194. The feedback loop is thus used to move the plunger 148 appropriately to maintain a constant pressure in the balloon.

It is not uncommon to encounter a clot that may be broken more than once as a balloon catheter stretches it. FIG. 10 shows a graph 185 where a plurality of "pops" are encountered at 190*a*, 190*b*, and 190*c*. Here the program segment loaded into the computer 106 either specified a maximum pressure to be achieved, or a maximum volume to be achieved, given the pressure and volume limits of the balloon and/or the size constraints of the vessel. Alternatively, the program segment allows the device to be used in a manual mode, with safety limits set on pressure and volume. In manual mode the physician uses a hand control 196 (FIG. 3) to control the inflation of the balloon, while viewing the display 183 for visual indication of the occurrence of a "pop" at 190. Additional stimuli may be provided to the physician such as a tactile feedback mechanism, such as a vibration or a proportional force feedback, in the hand control 196, or an audible tone provided by a speaker in the display 183. Additionally, a program segment may be provided that allows a physician to inflate the balloon manually, while "recording" flow rates, volumes and pressures used, so that the computer 106 may "learn" how the physician inflated the balloon. The physician may then instruct the computer 106 to repeat the inflation techniques he or she just performed. There are many instances where multiple inflations must be performed and this feature allows the physician to replicate a desired inflation automatically.

FIG. 8 shows a dotted line 188 that represents a baseline pressure profile of a particular balloon catheter in a no-load environment. One aspect of the present invention provides a bar code reader 198 (FIG. 7), or similar data input device, that is useable to input a pressure profile. The balloon catheter manufacturer supplies the profile, preferably as a bar code on the catheter packaging, of the baseline no-load inflation characteristics of the balloon catheter contained therein.

Knowing the baseline pressure characteristics of the balloon catheter allows the physician to view the difference between the actual, loaded pressure plot and the baseline graph 188. The difference is attributed to the resistance to inflation exhibited by the blood vessel.

The foregoing description addresses embodiments encompassing the principles of the present invention. The embodiments may be changed, modified and/or implemented using various types of arrangements. Those skilled in the art will readily recognize various modifications and changes that may be made to the invention without strictly following the exemplary embodiments and applications illustrated and described herein, and without departing from the scope of the invention, which is set forth in the following claims.

What is claimed is:

1. An automatic medical balloon inflation device comprising:
   a fluid pump attachable to a balloon catheter and configured to provide fluid pressure to a balloon at a distal end of the balloon catheter, wherein the balloon catheter is associated with baseline pressure data that is representative of inflation characteristics of the balloon catheter under a no-load condition;
   a computer configured to control the fluid pressure created by the fluid pump; and
   a pressure sensor operably attached to the computer and configured to provide data to the computer corresponding to the fluid pressure created by the fluid pump,
   wherein prior to the fluid pump providing the fluid pressure to the balloon for a balloon inflation procedure, the computer is configured to receive computer-readable data associated with the balloon catheter comprising the baseline pressure data that is representative of the inflation characteristics of the balloon catheter under the no-load condition, and
   wherein when the fluid pump provides the fluid pressure to the balloon during the balloon inflation procedure, the computer is configured to compare the baseline pressure data to the data received by the computer from the pressure sensor corresponding to the fluid pressure created by the fluid pump.

2. The automatic medical balloon inflation device of claim 1 further comprising a program segment, stored in a computer readable medium readable by the computer, that when executed enables the computer to determine an existence of predetermined characteristics of the data received by the computer from the pressure sensor, and to react to the characteristics in a predetermined manner.

3. The automatic medical balloon inflation device of claim 1 further comprising a bar code reader useable to upload the baseline pressure data to the computer.

4. The automatic medical balloon inflation device of claim 1, wherein the computer is further configured to shut down the inflation device if the comparison indicates a safety issue associated with the balloon catheter.

5. The automatic medical balloon inflation device of claim 1, wherein the computer is further configured to hold the fluid pressure created by the pump at a predetermined level based upon the comparison.

6. The automatic medical balloon inflation device of claim 1 further comprising a monitor operably connected to the computer and capable of displaying data representative of the data received from the pressure sensor.

7. The automatic medical balloon inflation device of claim 6 further comprising a program segment, stored in a computer readable medium readable by the computer, that when executed enables the computer to send signals to the monitor to display a graph of fluid pressure versus time.

8. The automatic medical balloon inflation device of claim 6 further comprising a program segment, stored in a computer readable medium readable by the computer, that when executed enables the computer to send signals to the monitor to display a graph of balloon volume versus time.

* * * * *